(12) United States Patent
Baraldi et al.

(10) Patent No.: US 7,964,642 B2
(45) Date of Patent: Jun. 21, 2011

(54) VANILLOID TRPV1 RECEPTOR ANTAGONISTS

(75) Inventors: Pier Giovanni Baraldi, Ferrara (IT); Pier Andrea Borea, Ferrara (IT); Pierangelo Geppetti, Ferrara (IT)

(73) Assignee: Pharmeste S.R.L. (IT)

( * ) Notice: Subject to any disclaimer, the term of this patent is extended or adjusted under 35 U.S.C. 154(b) by 987 days.

(21) Appl. No.: 11/570,758

(22) PCT Filed: Jun. 16, 2005

(86) PCT No.: PCT/EP2005/006471
§ 371 (c)(1),
(2), (4) Date: Dec. 15, 2006

(87) PCT Pub. No.: WO2005/123666
PCT Pub. Date: Dec. 29, 2005

(65) Prior Publication Data
US 2008/0085936 A1    Apr. 10, 2008

(30) Foreign Application Priority Data

Jun. 18, 2004 (IT) .............................. MI2004A1231

(51) Int. Cl.
*A61K 31/17* (2006.01)
*C07C 335/12* (2006.01)
*C07C 335/16* (2006.01)

(52) U.S. Cl. .......... 514/586; 514/587; 514/595; 564/27; 564/28; 564/56

(58) Field of Classification Search ................... 514/586, 514/587, 595; 564/27, 28, 56
See application file for complete search history.

(56) References Cited
FOREIGN PATENT DOCUMENTS
WO    WO 02/16318 A    2/2002

OTHER PUBLICATIONS

Daqiang X et al: "Reductive Alkylation of Urea: A practical Route to Substituted Ureas" Tetrahedron Letter, Elsevier, Amsterdam, NL, vol. 39, No. 10, Mar. 5, 1998, pp. 1107-1110, XP004109129 ISSN: 0040-4039 table 2.
Suh et al: "Novel non-vanilloid VR1 Antagonist of High Analgesic Effects and its Structural Requirement for VR1 Antagonist Effects" Bioorrganic & Medicinal Chemistry Letter, vol. 13, 2003, pp. 4389-4393, XP009057761 example 17.
Parl et al: N-4-Methansulfonamidobenzyl-N-2-substituted-4-tert-butyl-benzyl thioureas as potent vanilloid receptor antagonistic ligands Bioorganic & Medicinal Chemistry Letter, vol. 14, 2004, pp. 1693-1696, XP009057760 table 1.
International Search Report PCT/EP2005/006471 dated Nov. 25, 2005.
José Barluenga, et al "Acid-Mediated Reaction of Bis(pyridine) iodoniurn(I) Tetrafluoroborate With Aromatic Compounds. A Selective and General Iodination Method," J. Org. Chem., vol. 58, (1993), pp. 2058-2060.
José Barluenga, et al., "Iodination of Aromatic Residues in Peptides by Reaction With $IPy_2BF_4$," Chem. Commun., (1996), pp. 1505-1506.
Roger Wrigglesworth, et al., "Analogues of Capsaicin With Agonist Activity as Novel Analgesic Agents: Structure-Activity Studies. 4. Potent, Orally Active Analgesics," J. Med. Chem., vol. 39, (1996), pp. 4942-4951.
Michela Rigoni, et al., "Neurogenic Responses Mediated by Vanilloid Receptor-1 (TRPV 1) Are Blocked by the High Affinity Antagonist, Iodo-Resmiferatoxin," British Journal of Pharmacology, vol. 138, (2003), pp. 977-985.
Yoshihisa Kudo, et al., "Monitoring of Intracellular $Ca^{2+}$ Elevation in a Single Neural Cell Using a Fluorescence Microscope/Video-Camera System," Japanese Journal of Pharmacology, vol. 41, (1986), pp. 345-351.

*Primary Examiner* — Peter G O'Sullivan
(74) *Attorney, Agent, or Firm* — Ostrolenk Faber LLP

(57) ABSTRACT

The invention relates to compounds of formula (I), wherein R, $R_1$, $R_2$, X and n are as defined in the description, and their use for the preparation of pharmaceutical compositions for the treatment of inflammatory states.

7 Claims, No Drawings

VANILLOID TRPV1 RECEPTOR ANTAGONISTS

CROSS REFERENCE TO RELATED APPLICATIONS

The present application is a 35 U.S.C. §371 National Phase conversion of PCT/EP2005/006471 filed Jun. 16, 2005, which claims priority of Italian Application No. MI2004A 001231 filed Jun. 18, 2004.

FIELD OF THE INVENTION

The present invention relates to antagonists of the vanilloid receptor, in particular benzylamides that antagonize the vanilloid TRPV1 receptor.

STATE OF THE ART

Recent experimental evidences have demonstrated that the expression of the vanilloid TRPV1 receptor (transient receptor potential channel) increases in the course of inflammatory states. This led to suggest that vanilloid receptor antagonists could be useful for the treatment of such states, for example chronic pain or inflammatory hyperalgesia.

A number of vanilloid receptor antagonists are known; some of them derive from capsaicin and are referred to as capsaicinoid antagonists. In particular, Sandoz disclosed (Wrigglesworth, R. et al, *J. Med. Chem.* 1996, 39, 4941-4951) the thiourea of formula (II):

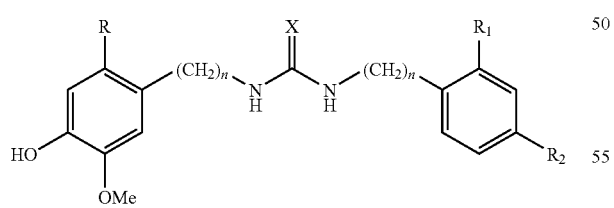

(II)

DESCRIPTION OF THE INVENTION

The present invention relates to compounds of formula (I)

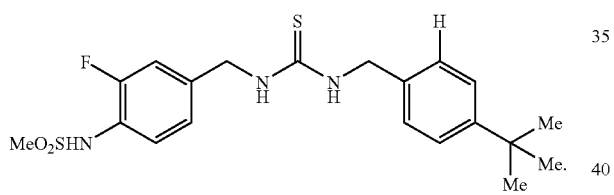

(I)

wherein
R is halogen;
$R_1$ is H, halogen, methoxy, ethoxy, trifluoromethyl, nitro, amino;
$R_2$ is tert-butyl or trifluoromethyl;
n is an integer selected from 0, 1 or 2;
X is O or S.
The term "halogen" indicates an halogen selected from fluorine, chlorine, bromine or iodine.

A first preferred group of compounds of formula (I) is that wherein:
X is S;
n is 1;
$R_2$ is tert-butyl.
Among them, particularly preferred are compounds (Ia), wherein R is iodine and $R_1$ is hydrogen and (Ib) wherein R is chlorine and $R_1$ is hydrogen.
A second preferred group of compounds is that wherein:
X is S;
n is 1;
$R_2$ is trifluoromethyl.
Among them particularly preferred is the compound of formula (Ic), wherein R is iodine and $R_1$ is hydrogen.
The compounds of formula (I) can be prepared by means of conventional methods, such as the reaction of a compound of formula (III)

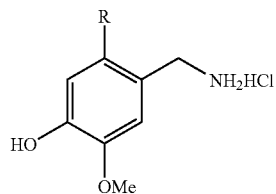

(III)

wherein R is as defined above and the hydroxy group is protected with an acetyl, benzyl or benzoyl group,
with a compound of formula (IV)

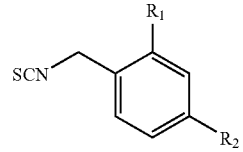

(IV)

wherein $R_1$ and $R_2$ are as defined above.
The compounds of formula (I) are able to inhibit the vanilloid TRPV1 receptor and can be used for the preparation of pharmaceutical compositions for the treatment of inflammatory states, such as chronic pain and inflammatory hyperalgesia. These formulations can be prepared by conventional methods and excipients, such as those disclosed in Remington's Pharmaceutical Sciences Handbook, XVII ed. Mack Pub., N.Y., U.S.A.
The invention will be hereinafter illustrated by means of the following examples and schemes 1 and 2.

EXAMPLES

The Examples are provided only for the purpose of illustrating the invention and are not to be deemed as limiting the invention in any manner.

The reactions were routinely monitored by thin-layer chromatography (TLC) on silica gel (precoated $F_{245}$ Merck plates) and the products visualized with an iodine or potassium permanganate solution. $^1$H NMR spectra were recorded in $CDCl_3$, $CF_3COOD$ or DMSO-$d_6$ with a Bruker AC 200 spectrometer. Peak positions are given in parts per million ($\delta$) downfield from tetramethylsilane as internal standard, and J values are given in Hz. IR spectra were recorded on a Pye Unicam SP 300 spectrometer using the KBr Wafer technique. Mass spectra were obtained with a Shimadzu QP5050 DI 50 spectrometer. The expression "Light petroleum ether" refers to petroleum fraction boiling at 40-60° C. Melting points (M.p.) were determined on a Buchi-Tottoli instrument and are uncorrected. Chromatographies were performed using Merck 60-200 mesh silica gel. The synthesized compounds showed $^1$H NMR spectra in agreement with the assigned structures. Elemental analyses were within ±0.4% of the theoretical values for C, H, and N.

Example 1

1-(4-tert-butyl)-3-(2-iodo-4-hydroxy-5-methoxy benzyl) thiourea Ia 1.1. Synthesis of 4-acetyloxy-3-methoxy-N-acetyl-benzylamine Acetic anhydride (1 ml, 10.5 mmol) was added to a solution of 4-hydroxy-3-methoxy-benzylamine hydrochloride (0.5 g, 2.63 mmol) in pyridine (5 ml) and the mixture was stirred at room temperature for 6 hours. The solvent was removed under reduced pressure and the residue was suspended in water (100 ml). The aqueous layer was extracted with ethyl acetate (3×20 ml) and the combined organic phases were anhydrified ($Na_2SO_4$) and evaporated under reduced pressure to afford the title compound as white solid (0.45 g, yield 75%).

$^1$H-NMR($CDCl_3$) δ 2.01 (s, 3H, $CH_3$), 2.31 (s, 3H, $CH_3$), 3.81 (s, 3H, $OCH_3$), 4.38 (d, 2H, J=6, $CH_2$), 5.90 (bs, 1H, NH), 6.90 (m, 3H, aromatic).

MS: m/z 238.1 ($M^+$ $C_{12}H_{15}NO_4$).

1.2. Synthesis of 2-iodo-4-acetyloxy-5-methoxy-N-acetyl benzyl amine

The diacetyl derivative of example 1.1 and a catalytic amount of trifluoromethane sulfonic acid (5-6 drops) were added to a solution of $IPy_2BF_4$[1,2] (0.69 g, 6.9 mmol) in $CH_2Cl_2$ (40 ml). The resulting mixture was stirred at room temperature for 5 hours, then added with 10% aq. sodium thiosulfate until it became completely clear. The aqueous layer was extracted with $CH_2Cl_2$ (3×25 ml) and the organic phases were anhydrified ($Na_2SO_4$) and evaporated under vacuum. The residue was recrystallized from a mixture of $CH_2Cl_2/Et_2O$ to afford the title compound as pale yellow solid (0.38 g, yield 65%).

$^1$H-NMR($CDCl_3$) δ 2.06 (s, 3H, $CH_3$), 2.33 (s, 3H, $CH_3$), 3.82 (s, 3H, $OCH_3$), 4.41 (d, 2H, J=5.6, $CH_2$), 6.0 (t, 1H, NH), 7.04 (s, 1H, aromatic), 7.44 (s, 1H, aromatic).

Bidimensional NOESY ($CDCl_3$): coupling between the singlet at 7.44 ppm and the singlet at 2.33 ppm confirms that iodine is at the 2-position of the aromatic ring.

MS: m/z 364 ($M^+$ $C_{12}H_{14}INO_4$).

1.3. Synthesis of 2-iodo-4-hydroxy-5-methoxy-benzylamine hydrochloride

37% hydrochloric acid (0.2 ml) was added to a solution of 2-iodo-4-acetyloxy-5-methoxy-N-acetyl-benzylamine (0.1 g, 0.27 mmol) in abs. ethanol (5 ml) and the mixture was refluxed for 12 hours. After cooling, the solvent was evaporated off under reduced pressure and the residue was recrystallized from dry acetone to afford the title compound as pale yellow solid in quantitative yield.

$^1$H NMR(DMSO-$d_6$) δ 3.80 (s, 3H, $OCH_3$), 3.97 (m, 2H, $CH_2$), 7.21 (s, 1H, aromatic), 7.29 (s, 1H, aromatic), 8.46 (bs, 3H, $NH_3^+$), 9.38 (bs, 1H, OH).

M.p.: >300° C.

MS: m/z 315.9 ($M^+$ $C_8H_{11}ClINO_2$).

1.4. Synthesis of 1-(4-tert-butyl)-3-(2-iodo-4-hydroxy-5-methoxybenzyl) thiourea Ia Reagents: (i) 4-tert-butylbenzyl isothiocyanate[3], TEA, DMF, rt TEA (0.95 mmol, 0.13 ml) and 4-tert-butyl isothiocyanate[3] (0.47 mmol, 0.1 g) were added to a suspension of 2-iodo-4-hydroxy-5-methoxybenzylamine hydrochloride (0.15 g, 0.47 mmol) in dry DMF (10 ml). The mixture was stirred at room temperature for 20 hours and the residue was added with water (30 ml). The aqueous layer was extracted with ethyl acetate (3×20 ml) and the combined organic phases were anhydrified ($Na_2SO_4$), then evaporated under reduced pressure. The residue was purified by flash chromatography (1:1 ethyl acetate/light petroleum) to afford Ia as white solid (60 mg, 32% yield).

$^1$H NMR(DMSO-$d_6$) δ 1.26 (s, 9H, tert-butyl), 3.67 (s, 3H, $OCH_3$), 4.50 (d, 2H, J=4, $CH_2$), 4.62 (d, 2H, J=4.2, $CH_2$), 6.90 (bs, 1H, aromatic), 7.18 (s, 1H, aromatic), 7.22 (d, 2H, J=4.1, aromatic), 7.33 (d, 2H, J=4.2, aromatic), 7.70 (bs, 1H, NH), 7.91 (bs, 1H, NH), 9.3 (s, 1H, OH).

IR (KBr) $cm^{-1}$: 1547 (C=S).

M.p.: 194-5° C.

MS: m/z 485.4 ($M^+$ $C_{20}H_{25}IN_2O_2S$).

Anal. C, H, N, O ($C_{20}H_{25}IN_2O_2S$): calculated :C, 49.59; H, 5.20; N, 5.78; O, 6.61. Found: C, 49.45; H, 5.11; N, 5.62; O, 6.57.

Example 2

Synthesis of 1-(4-tert-butyl)-3-(2-chloro-4-hydroxy-5-methoxybenzyl) thiourea Ib 2.1. Synthesis of 2-chloro-4-acetyloxy-5-methoxy-N-acetyl benzyl amine 2b N-chlorosuccinimide (3.15 mmol, 0.42 g) was added to a solution of 4-acetyloxy-3-methoxy-N-acetyl-benzylamine of Example 1.1 (0.5 g, 2.1 mmol) in dry DMF (6 ml) and the mixture was stirred for 30' at 0° C. and then for 16 hours at room temperature.

When water was added to the reaction (40 ml) the formation of a white precipitate was observed.

The solid was filtered off and washed twice with cold water (2×20 ml), then dried over $P_2O_5$ to afford the title compound as white solid (0.45 g, 83% yield).

$^1$H NMR(DMSO-$d_6$) δ 1.89 (s, 3H), 2.24 (s, 3H), 3.76 (s, 3H, $OCH_3$), 4.27 (d, 2H, $CH_2$, J=8), 7.09 (s, 1H, aromatic), 7.25 (s, 1H, aromatic), 8.35 (t, 1H, NH).

Bidimensional NOESY (DMSO-$d_6$): coupling between the singlet at 2.24 ppm and the singlet at 7.25 ppm confirms that chlorine is at the 2-position of the aromatic ring.

MS: m/z 272.1 ($M^+$ $C_{12}H_{14}ClNO_4$).

2.2. Synthesis of 2-chloro-4-hydroxy-5-methoxy-benzylamine hydrochloride 3b

37% hydrochloric acid (2.5 ml) was added to a solution of 2-chloro-4-acetyloxy-5-methoxy-N-acetyl-benzylamine 2b (0.45 g, 1.66 mmol) in abs. ethanol (15 ml) and the mixture was refluxed for 12 hours. The reaction was cooled and the solvent was evaporated under reduced pressure. The residue was recrystallized from dry acetone to afford the title compound as white crystals in quantitative yield.

$^1$H NMR(DMSO-$d_6$) δ 3.87 (s, 3H, OCH$_3$), 4.00 (m, 2H, CH$_2$), 6.91 (s, 1H, aromatic), 7.32 (s, 1H, aromatic), 8.46 (bs, 3H, NH$_3^+$), 9.80 (bs, 1H, OH).

M.p.: >300° C.

2.3. Synthesis of 1-(4-tert-butyl)-3-(2-chloro-4-hydroxy-5-methoxybenzyl) thiourea Ib TEA (0.98 mmol, 0.14 ml) and 4-tert-butyl isothiocyanate[3] (0.54 mmol, 0.11 g) were added to a suspension of 2-chloro-4-hydroxy-5-methoxybenzylamine hydrochloride 3b (0.11 g, 0.49 mmol) in dry DMF (10 ml). The mixture was stirred at room temperature for 18 hours, then the solvent was removed under reduced pressure and the residue was purified by flash chromatography (4:6 ethyl acetate/light petroleum) to afford Ib as pale yellow solid (65 mg, 42% yield).

$^1$H NMR(DMSO-$d_6$) δ 1.25 (s, 9H, tert-butyl), 3.68 (s, 3H, OCH$_3$), 4.59 (m, 4H, CH$_2$), 6.80 (s, 1H, aromatic), 6.91 (s, 1H, aromatic), 7.23 (d, 2H, J=9.8, aromatic), 7.35 (d, 2H, J=9.7, aromatic), 7.65 (bs, 1H, NH), 7.92 (bs, 1H, NH), 9.47 (s, 1H, OH).

IR (KBr) cm$^{-1}$: 1562 (C=S).

M.p.: 192-3° C.

MS: m/z 393.3 (M$^+$ C$_{20}$H$_{25}$ClN$_2$O$_2$S).

Anal. C, H, N, O (C$_{20}$H$_{25}$ClN$_2$O$_2$S): calculated: C, 61.13; H, 6.41; N, 7.13; O, 8.14. Found: C, 61.04; H, 6.38; N, 7.04; O, 61.00.

Example 3

Synthesis of 1-(4-trifluoromethyl)-3-(2-iodo-4-hydroxy-5-methoxybenzyl) thiourea Ic TEA (0.95 mmol, 0.13 ml) and 4-trifluoromethyl isothiocyanate[3] (0.47 mmol, 0.103 g) were added to a suspension of 2-iodo-4-hydroxy-5-methoxybenzylamine hydrochloride (0.15 g, 0.47 mmol) in dry DMF (10 ml). The mixture was stirred at room temperature for 18 hours, then the solvent was removed under reduced pressure and the residue was purified by flash chromatography (1:1 ethyl acetate/light petroleum) to afford Ic as pale yellow solid (90 mg, 40% yield).

$^1$H NMR(DMSO-$d_6$) δ 3.74 (s, 3H, OCH$_3$), 4.63 (bs, 2H, CH$_2$), 4.76 (d, 2H, J=4.2, CH$_2$), 6.96 (s, 1H, aromatic), 7.10 (bs, 1H, NH), 7.22 (s, 1H, aromatic), 7.36 (d, 2H, J=4.1, aromatic), 7.48 (d, 2H, J=4.2, aromatic), 7.70 (bs, 1H, NH), 8.01 (bs, 1H, OH).

IR (KBr) cm$^{-1}$: 1558 (C=S).

M.p.: 208-210° C.

MS: m/z 497.2 (M$^+$ C$_{17}$H$_{16}$F$_3$IN$_2$O$_2$S).

Anal. C, H, N, 0 (C$_{17}$H$_{16}$F$_3$IN$_2$O$_2$S): calculated: C, 41.14; H, 3.25; N, 5.64; O, 6.45. Found: C, 40.98; H, 3.19; N, 5.57; O, 6.42.

Biological Assay

Newborn and adult Sprague-Dawley rats (~250 g) were used (Harlam, Italy). All experiments complied with the national guidelines and were approved by the regional ethics committee.

Ca$^{2+}$ Fluorescence Measurements in Cultured Rat Trigeminal Ganglia

Newborn rats (2 days old) were terminally anaesthetized and decapitated. Trigeminal ganglia were removed and rapidly placed in a cold phosphate buffered solution (PBS) before being transferred to collagenase/dispase (1 mg/ml dissolved in Ca$^{2+}$-Mg$^{2+}$-free PBS) for 35 min. at 37° C.[4]

After the enzymatic treatment the ganglia were rinsed three times with Ca$^{2+}$-Mg$^{2+}$-free PBS and then placed in 2 ml of cold DMEM supplemented with 10% foetal bovine serum (FBS, heat inactivated), 2 mM L-glutamine, 100 μ/ml penicillin and 100 mg/ml streptomycin. The ganglia were then dissociated into single cells by several passages through a series of syringe needles (23 G down to 25 G). Finally, the medium and ganglia cells sieved through a 40 mm filter to remove debris and taken up with 8 ml of DMEM medium and centrifuged (200×g for 5 min.). The final cell pellet was re-suspended in DMEM medium (supplemented with 100 ng/ml mouse Nerve Growth Factor (mouse-NGF-7S) and cytosine-β-D-arabino-furanoside free base (ARA-C) 2.5 mM). The cells were plated on poly-L-lysine (8.3 mM) and laminin (5 mM) coated 25 mm glass cover slips and kept for 2 to 5 days at 37° C. in a humidified incubator gassed with 5% CO$_2$ and air. Plated neurons were loaded with Fura-2-AM-ester (3 μM) in Ca$^{2+}$ buffer solution of the following composition (mM): CaCl$_2$ 1.4, KCl 5.4, MgSO$_4$ 0.4, NaCl 135, D-glucose 5, HEPES 10 with BSA 0.1%, at pH 7.4, for 40 min at 37° C., washed twice with the Ca$^{2+}$ buffer solution and transferred to a chamber on the stage of a Nikon eclipse TE300 microscope. The dye was excited at 340 and 380 nm to indicate relative [Ca$^{2+}$]$_i$ changes by the $F_{340}/F_{380}$ ratio recorded with a dynamic image analysis system (Laboratory Automation 2.0, RCS, Florence, Italy). Capsaicin (0.1 μM) and ionomycin (5 μM) were added to the chamber. A calibration curve using a buffer containing Fura-2-AM-ester and determinant concentrations of free Ca$^{2+}$ was used to convert the obtained data from $F_{340}/F_{380}$ ratio to [Ca$^{2+}$]$_i$ (nM)[5].

The effects of Ia, Ib and Ic were tested against capsaicin-induced calcium mobilisation; Ia, Ib and Ic were incubated for 10 minutes prior to the capsaicin challenge. The inhibitory effect of the reference TRPV1 antagonist, capsazepine, was also tested.

Wiping Test in Rats

The irritant effect (induction of wiping movements) of capsaicin was assessed by applying capsaicin 0.1% (50 μl) on the rat conjunctiva and the number of wiping movements was recorded during the 60 s period that followed the application. In another set of experiments, the rats were treated intraperitoneally with different doses of Ia and Ic and capsaicin-induced wiping was studied.

Drugs and Solubility

Drugs and reagents were obtained from the indicated companies: capsaicin, ionomycin, laminin, poly-L-lysine and capsazepine from Sigma, Italy; mouse NGF-7S and collagenase/dispase from Roche Diagnostics, Italy; Dulbecco's Modified Eagle's medium (DMEM), foetal bovine serum (FBS) heat inactivated, L-glutamine (200 mM), penicillin/streptomycin (10,000 IU/ml±10,000 UG/ml), Ca$^{2+}$-Mg$^{2+}$-free phosphate buffered solution (PBS) from Gibco, Italy; Fura-2-AM-ester from Società Italiana Chimici, Italy. Stock solutions of capsaicin (10 mM) were prepared in 100% ethanol. Mother solutions of Ia (100 mM), Ib (100 mM), Ic (100 mM), Fura-2-AM-ester (100 mM) and ionomycin (100 mM) were prepared in DMSO. Appropriate dilutions were then made in Krebs buffer solution.

Results:

Ca$^{2+}$ Fluorescence

Capsaicin (0.1 μM) caused an increase in [Ca$^{2+}$]$_i$ in the vast majority (95%) of rat trigeminal neuronal cells, that therefore were identified as TRPV1 expressing neurons. The threshold concentrations of Ia, Ib and Ic that produced an inhibitory effect were 0.1 nM, 0.1 nM and 1 nM respectively. Complete inhibition of the response to capsaicin was obtained with 0.1 μM Ia and 3 μM Ic. IC$_{50}$ values of Ia, Ib and Ic inhibiting capsaicin-evoked $[Ca^{2+}]_i$ mobilization were 3.48 (1.46-8.30) nM, 3.86 (2.13-7.0) nM and 70 (50-98) nM, respectively. The reference TRPV1 antagonist, capsazepine, inhibited the capsaicin response with an $IC_{50}$ of 2344 (2090-2659) nM. Mobilization of $[Ca^{2+}]_i$ evoked by 5 mM KCl was not affected by Ia, Ib and Ic. The results are expressed as Mean and 95% fiducial limits.

Wiping Test in Rats

Intraperitoneal Ia and Ic, 15 minutes prior to the capsaicin challenge, significantly reduced capsaicin-induced wiping in rats. The $ED_{50}$ values were 2.76 (2.05-3.35) mg/kg for Ia and 7.20 (6.34-7.89) mg/kg for Ic.

Conclusions

In in vitro and in vivo studies, Ia, Ib and Ic were able to inhibit TRPV1 activated responses with an affinity that was significantly greater than that of capsazepine, therefore they can be conveniently used for the preparation of medicaments for the treatment of pain.

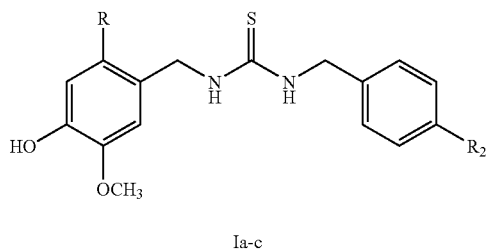

Ia-c

Reagents: (i) 4-tert-butyl isothiocyanate or 4-trifluoromethyl isothiocyanate[3], TEA, DMF, rt.
Ia: R = I, $R_2$ = tert-butyl
Ib: R = Cl, $R_2$ = tert-butyl
Ic: R = I, $R_2$ = trifluoromethyl Scheme 1:

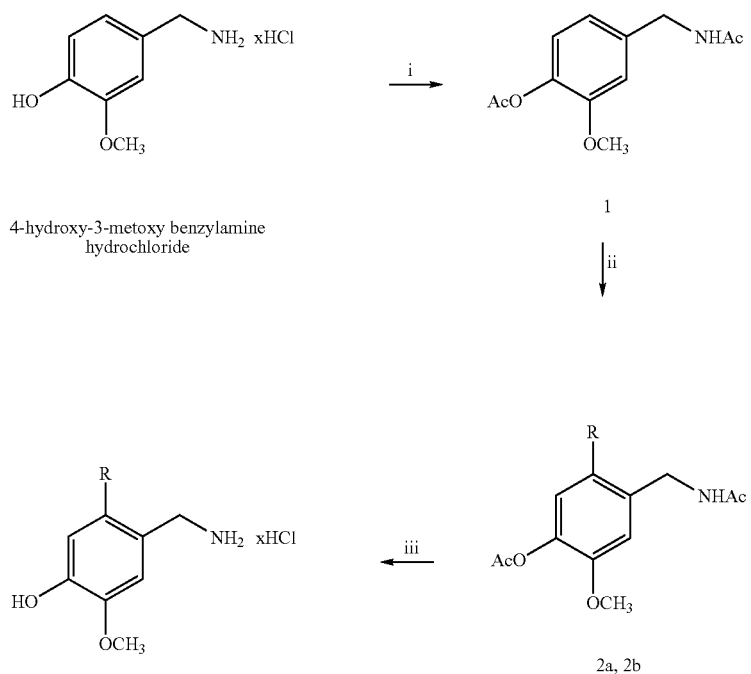

4-hydroxy-3-metoxy benzylamine hydrochloride

Reagents: i) Acetic anhydride, pyridine, rt; ii) $IPy_2BF_4$, $CF_3SO_3H$ or NCS, DMF; iii) HCl 37%, EtOH, rfx.
a R = I; b R = Cl Scheme 2: Synthesis of compounds Ia, Ib, Ic

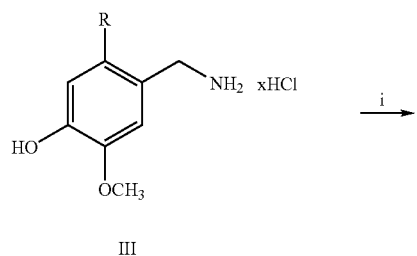

III

REFERENCES

1. Barluenga, J.; Gonzales, J. M.; Garcia-Martin, M. A.; Campos, P. J.; Asensio, G. J. Org. Chem. 1993, 58, 2058-2060.
2. Barluenga, J.; Garcia-Martin, M. A.; Gonzales, J. M.; Clapes, P.; Valencia, G. Chem. Commun. 1996, 1505-1506.
3. Wrigglesworth, R.; Walpole, C. S. J.; Bevan, S.; Campbell, E. A.; Dray, A.; Hughes, G. A.; James, I.; Masdin, K. J.; Winter, J. J. Med. Chem. 1996, 39, 4942-4951.
4. Rigoni M. et al., British Journal of Pharmacology, 2003, 138, 977-985.
5. Kudo Y. et al., Japanese Journal of Pharmacology, 1986, 41, 345-151.

What is claimed is:

1. Compounds of formula (I)

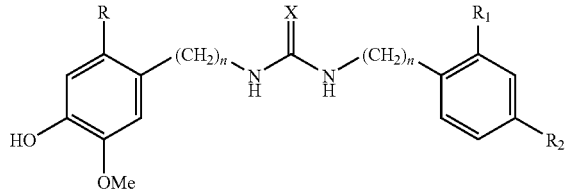

wherein
R is halogen selected from fluorine, chlorine, bromine and iodine;
R₁ is selected from H, halogen selected from fluorine, chlorine, bromine and iodine, methoxy, ethoxy, trifluoromethyl, nitro and amino;
R₂ is trifluoromethyl;
n is 1; and
X is S.

2. A compound according to claim 1 wherein R is iodine and R₁ is hydrogen.

3. A compound according to claim 1 wherein R is chlorine and R₁ is hydrogen.

4. A medicament comprising a compound of formula (I) as defined in claim 1.

5. A vanilloid receptor antagonist comprising a compound of formula (I) as defined in claim 1.

6. A method of preparing a pharmaceutical composition for the therapy of inflammatory states, which method comprises adding to said composition a compound of formula (I) as defined in claim 1.

7. A pharmaceutical composition containing compounds of formula (I) as defined in claim 1, in admixture with at least one of a pharmaceutically suitable excipient and a pharmaceutically suitable vehicle.

* * * * *